(12) United States Patent
Rodriguez Gutierrez

(10) Patent No.: US 12,426,980 B2
(45) Date of Patent: Sep. 30, 2025

(54) DENTAL OPERATORY PROTECTION TABLE

(71) Applicant: Roberto Mauricio Rodriguez Gutierrez, Amawalk, NY (US)

(72) Inventor: Roberto Mauricio Rodriguez Gutierrez, Amawalk, NY (US)

( * ) Notice: Subject to any disclaimer, the term of this patent is extended or adjusted under 35 U.S.C. 154(b) by 540 days.

(21) Appl. No.: 17/890,186

(22) Filed: Aug. 17, 2022

(65) Prior Publication Data
US 2022/0409323 A1 Dec. 29, 2022

Related U.S. Application Data

(63) Continuation of application No. 17/567,149, filed on Jan. 2, 2022, now abandoned, which is a continuation-in-part of application No. 17/330,344, filed on May 25, 2021, now abandoned.

(60) Provisional application No. 63/030,209, filed on May 26, 2020.

(51) Int. Cl.
| | | |
|---|---|---|
| *A61B 90/00* | (2016.01) |
| *A61B 90/40* | (2016.01) |
| *A61C 19/00* | (2006.01) |
| *A61M 16/00* | (2006.01) |
| *B08B 15/04* | (2006.01) |

(52) U.S. Cl.
CPC .............. *A61B 90/05* (2016.02); *A61B 90/40* (2016.02); *A61C 19/007* (2013.01); *A61M 16/009* (2013.01); *B08B 15/04* (2013.01)

(58) Field of Classification Search
CPC ... A61B 90/05; A61B 90/40; A61B 2090/401; A61B 6/04; A61C 17/065; A61G 10/005; A61G 15/10; A61G 13/00; A61G 15/00; A61F 5/00; A61M 16/009; B08B 15/04; B08B 15/02
See application file for complete search history.

*Primary Examiner* — Ophelia A Hawthorne
(74) *Attorney, Agent, or Firm* — Isaac Angres

(57) ABSTRACT

A protective apparatus for use in medical and dental procedures to prevent exposure and exchange of harmful substances between an area isolated by the apparatus and the environment of use. The apparatus includes a physical shield, a vacuum barrier, and an adjustable support frame. The apparatus further includes a vacuum connector for connecting the apparatus to a vacuum source, a vacuum conduit for flow communicating with the air around the perimeter of the physical shield such that the vacuum source draws air along with solid and liquid matter entrained in the air into the vacuum conduit, and a plurality of vacuum apertures located along the vacuum conduit for communicating the vacuum source with the air. The apparatus provides protection for persons in proximity to a source of harmful substances such as aerosols derived from patients infected with viruses or the like and more in particular corona viruses.

15 Claims, 12 Drawing Sheets

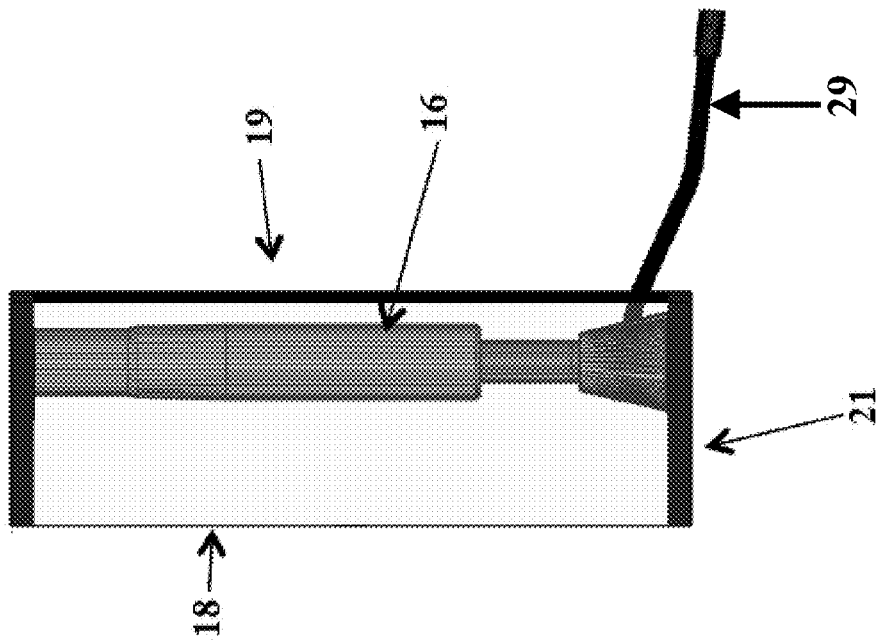
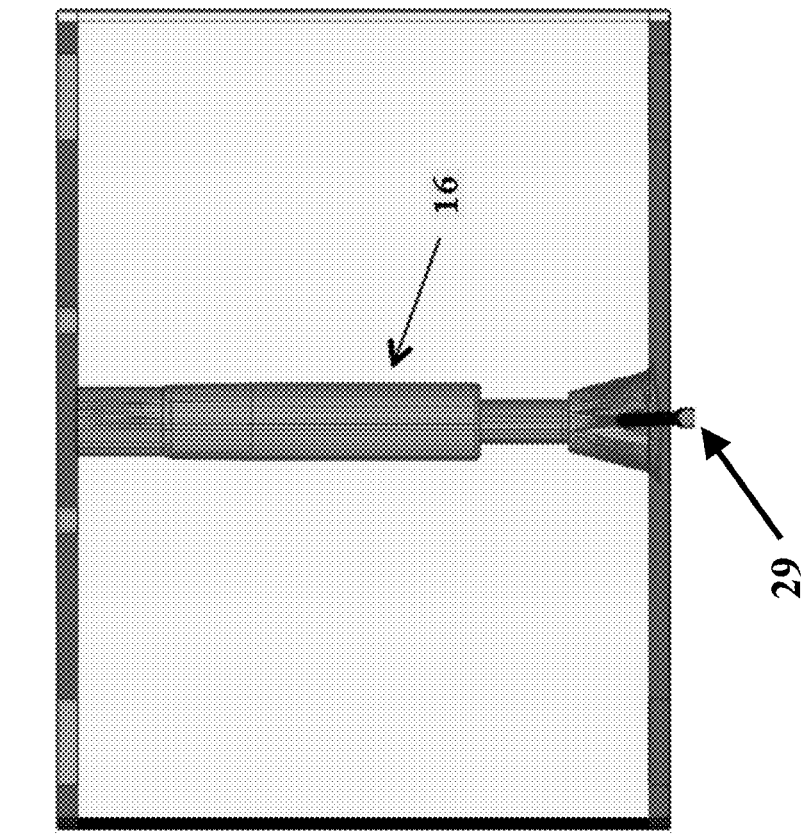

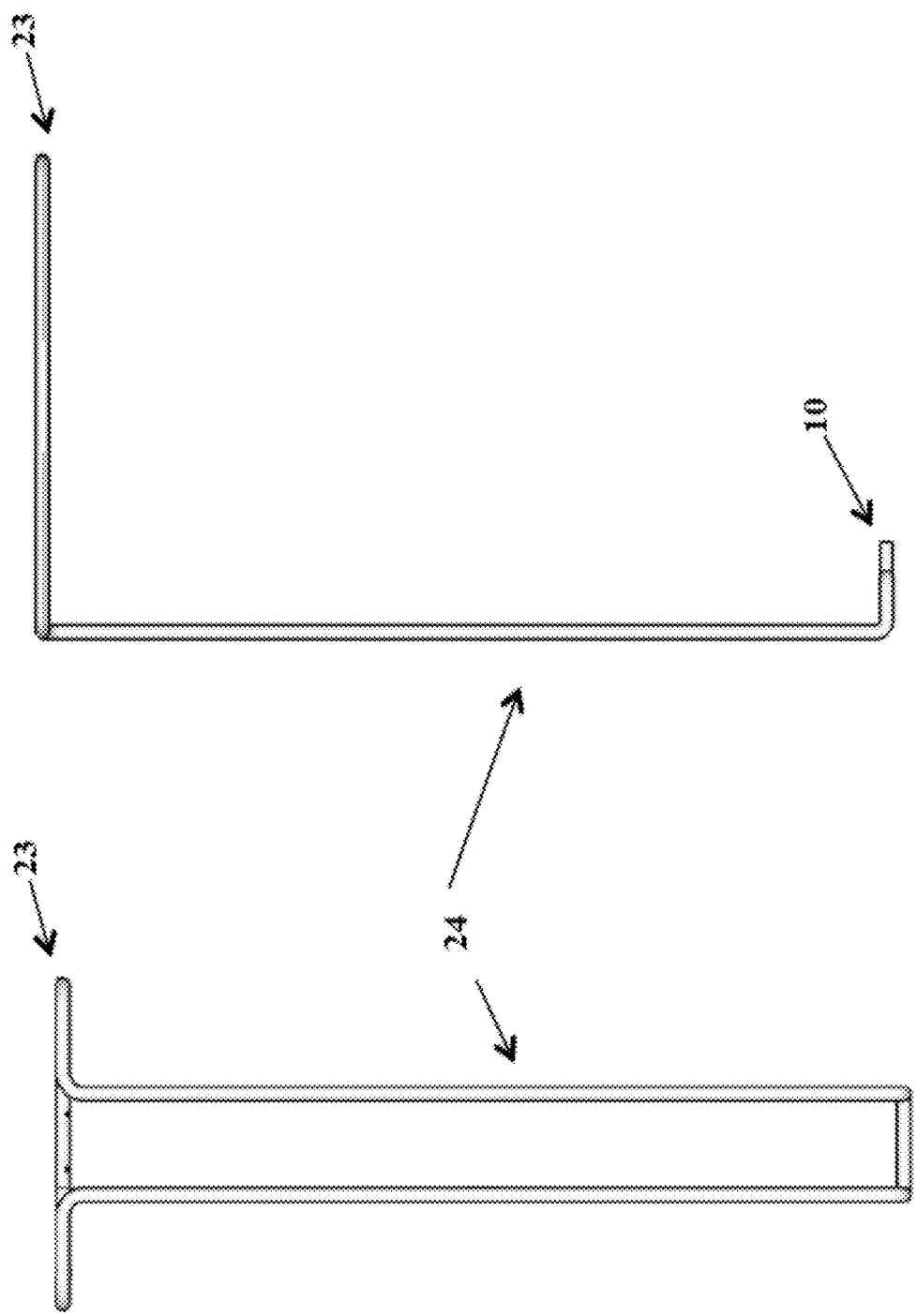

DENTAL OPERATORY PROTECTION TABLE

This application is a continuation of pending U.S. Ser. No. 17/567,149 filed Jan. 2, 2022; which application is a continuation-in-part application of pending U.S. Ser. No. 17/330,344 filed May 25, 2021. This application also claims the priority benefit under 35 U.S.C. section 119 of U.S. Provisional Patent Application No. 63/030,209 entitled "Dental Operatory Protection Table" filed on May 26, 2020; and which is in its entirety herein incorporated by reference.

FIELD OF THE INVENTION

The present invention is in the field of medical technology for protection of health care workers from infectious diseases. The instant invention relates to an apparatus and method for protection of both patient and healthcare provider from aerosol droplets that can be acquired during diagnosis and treatment without limiting the operator's movement or field of vision.

The present invention also relates to an integrated dental care apparatus which comprises at least a patient chair and a dental care mobile unit and to which is structurally connected at least one of the following: a shield for contamination protection, an instrument unit, a suction system of the integrated dental care apparatus, and optionally an arm for a display screen, an arm for an operation lamp, an arm for a tray, an arm for some other device or implement used in a dental care environment, a connector structure for any device or implement used in a dental care environment, whether mentioned above or not.

BACKGROUND OF THE INVENTION

During conventional dental procedures dental hygienists, dental assistants, dentists, orthodontists, and other people working directly with patients' open mouths run the risk of being exposed to infection through airborne bacteria or viruses dispersed in the mouth during different dental, medical, or other open mouth procedures. According to the Center for Disease Control, airborne bacteria and viruses is a pathway for the transmission of Severe Acquired Respiratory Syndrome (SARS), Tuberculosis (TB), measles, mumps, influenza, human immunodeficiency virus (HW), other viruses and bacteria, etc. The Center for Disease Control and the American Dental Association consensus has been that the greatest airborne infection threat in dentistry comes from the aerosols due to their ability to stay airborne and potential to enter respiratory passages. Any dental procedure with potential to aerosolize saliva and blood will spread infection bacteria or virus from the mouth, nose, throat, nasopharynx and respiratory tract. When dental procedures are being carried out, the use of some dental tools often cause aerosolization of saliva putting any people near the mouth at risk.

The current COVID-19 pandemic is transmitting at a historically unprecedented rate and is leaving disastrous global consequences in its wake. Its increased spread has induced heightened attention and efforts in the prevention of severe acute respiratory syndrome coronavirus 2 (SAR-CoV2) from the scientific, medical, and business communities—notwithstanding the general populous. Due to the increasing threat to global health, on Mar. 11, 2020, the World Health Organization (WHO) declared the COVID-19 crisis to be a global public health crisis.

Without question, in the US, the elegance and virulence of this strain have crippled the economy to an extent not witnessed since The Great Depression. Most unfortunately, COVID-19 is having a devastating impact on the lives and livelihoods of American citizens—US hospitals are inundated, front-line health workers are overburdened, PPE supplies are depleted, food supplies are threatened, and a disparate impact has been unleashed upon the nation's most vulnerable communities—including elderly, minority, and those in financially challenged or polluted high-density urban areas. While the transmission of SARS-CoV2 through relatively larger human respiratory droplets (via surfaces etc) and contact with infected persons are clear, the recognition of and concern regarding its aerosol transmission has been elevated exponentially—and justifiably so.

Due to the aforementioned modes of transmission, the CDC produced recommended guidelines for controlling the spread of the deadly SARS-CoV2 virus. A cornerstone of the CDC's guidelines is for the general public to maintain interpersonal social distancing of at least 6 ft. However, while this distancing benchmark may be effective for control of large viral droplet contact transmission, subsequent studies found that viral air clouds contaminated with the COVID-19 aerosols might travel much farther than the 6 feet CDC guideline. These expelled droplets can subsequently be inhaled, land in people's mucus membranes, and deposit onto surfaces where someone can touch them or be resuspended into the air. The aforementioned study published in the Journal of the American Medical Association found that, under the right conditions, liquid droplets from sneezes, coughs, and simple exhalations can travel more than 26 feet and linger in the air for a considerable time—risking someone walking through the cloud and becoming a viral host. The recent study focused on these turbulent gas clouds emitted when someone coughs, sneezes, or simply exhales. It was observed that liquid droplets of various sizes drop onto surfaces, while others can be trapped in a cloud that can swirl around a room with a payload of pathogen-bearing fine particulates for a significant amount of time. Many studies indicated that aerosols can remain suspended in the air for up to 4 hours and remain on some surfaces for up to 4 days.

Furthermore, the present invention relates to apparatus and devices for reducing or preventing the discharge of harmful substances and infectious germs such as viruses and bacteria from an area isolated by such a device to the surrounding environment.

Foreseeable applications for the present invention especially include the isolation of air contaminated by potentially disease-carrying blood or airborne aerosol bacterial and viral particles from a patient during examination or during a medical procedure, but can also include applications in laboratories, industrial environments and the like, where the isolation of an area for health and safety reasons is desirable and unobstructed manual access is necessary. In particular, such a device is needed where it is necessary for a surgeon, emergency room physician or other person to have generally open manual access to the area, yet where protection is required to prevent fluids such as blood from spraying into the face of the person and to prevent other fluids in the form of aerosols or the like and containing infectious material from escaping into the room surrounding the area.

The present invention is also especially useful in the medical area for preventing the escape of harmful bacterial or viral substances from the site of medical procedures such as surgical incisions, or respiratory aerosol releases and the like. Harmful substances of concern in the medical area include, but are not limited to, blood and other body fluids (which often form fine aerosols in the air during procedures requiring drilling or cutting), small particles of skin, fat or muscle tissue and bone particles which are contaminated. Such substances may be contaminated by hepatitis, acquired immune deficiency syndrome (AIDS), or other transmittable diseases. Medical procedures especially dangerous to operating room personnel are those using endoscopes and bone cutting devices such as drills, reamers, saws and similar devices which may cause harmful substances to become airborne. Such airborne substances may come in contact with an open cut, a mucous membrane, or the like of the medical practitioner such that the practitioner becomes infected or contaminated by the substances.

Currently, surgical garments and masks are used as the primary protection for operating room personnel. Surgical garments and masks are not intended to, and do not prevent, the spread of harmful substances and organisms to all parts of the general operating room environment and do not protect certain parts of the practitioner. For example, such equipment often does not protect the eyes and other exposed parts of the body of operating room personnel from contact with fluids in the form of airborne aerosols including bone particles and liquids or from direct sprays, streams, or splashes of liquids. Infections and contagious body fluids are of particular concern, especially in the region of the head.

A second category of protective devices in use in the medical area is protective hoods incorporating a vacuum system used to draw away anesthetic gases from the mouths of patients during oral surgery and dentistry. Typically, the hoods are mounted on the end of a free-standing boom or on an arm attached to a dentistry chair. In operation, the dentist or oral surgeon positions the hood over the mouth of the patient during or after administration of anesthesia and activates the vacuum generation means to evacuate the gases.

Such hoods are limited in use and there are numerous limitations in the ability of these hoods to be adapted to protect medical and dental personnel from airborne infectious material emanating from the patient in a general operating room environment.

First, the hoods are limited in size as they are intended to remove only the small amount of gases such as those present during oral surgery and dentistry. The small size of the hoods limits the adaptability thereof to provide a sufficient physical barrier to block streams and sprays of body fluids and to contain the airborne particles generated during large scale surgical procedures such as joint replacement. Enlarging the size of the physical barrier would generally require abandonment of the current support structure for one similar to that of the present invention. Additionally, the dental hoods have a centrally located vacuum system and do not provide vacuum around the periphery of the hood, providing only incomplete protection against the escape of harmful gases and the like. Again, enlarging of the size of the dental hoods for use in general surgery and the like would require substantial redesign of the evacuation system.

Second, the hoods are not completely or substantially transparent, generally containing only a small window, if transparent at all. If the hoods were enlarged for surgical use and the like, the visual obtrusiveness of the hoods would significantly impair the ability of surgeons and support staff to have unobstructed access to the incision, as maximum protection is afforded only when the hood is positioned in close proximity to the incision and extends over a wide area. Finally, as mentioned earlier, the hoods provide only a single vacuum aperture. A single vacuum aperture would not have the capability to provide a vacuum barrier around the perimeter of an area contemplated to be isolated and, consequently, it would be difficult to contain gases with such a device.

A third type of protective device in use in the medical area is an autopsy table incorporating a series of variable position vacuum ducts along the sides of the table, or alternatively, air supply ducts on one side of the table and vacuum ducts on the opposing side. In operation, the ducts draw a flow of air across the table so as to vent away noxious gases. At the head of the autopsy table, two opposing ducts may be positioned at the same height and a transparent table placed thereon.

Limitations of the autopsy table with respect to adaptability for the purposes of the present invention include the lack of vacuum ducts around the entire perimeter of the site of the medical procedure. Such openings in the vacuum barrier provide routes of escape for gases and aerosolized liquids not captured in the cross-flow due to obstructions of flow such as those occurring when persons reach into the cross-flow. Secondly, access to the site is limited on two sides due to the vacuum ducts and supplies that effectively form an access barrier. Additionally, the angle of the table is not variable and the configuration is not portable or free-standing.

Certain other conventional protective devices provide only a physical barrier or only a vacuum barrier but not a combination of the two. Those providing only a physical barrier generally are either too obtrusive to the surgeon's work area or do not prevent the escape of gases and vapors into the general operating room environment. For example, surgical garments that resemble astronaut's space suits which protect only the person wearing it provide no protection for the environment or others. Protective devices generating only vacuum to draw airborne substances, as is obvious, provide no physical barrier to streams or sprays of fluids.

Finally, vacuum devices currently in use and having self-contained vacuum source are often limited in application, as such devices incorporate no means for the containment, destruction, or safe evacuation of contaminants. Such devices are inappropriate for protection from hepatitis and AIDS as those viruses are dangerous in low concentrations and could be carried to remoter sites by an evacuation system that does not remove contaminants from the gas stream. Devices which merely dilute the concentration of toxic substances are clearly inadequate for the task of removal of infectious materials from the air.

Accordingly, there is a need for devices and apparatuses which aid in preventing splatter of liquids and aerosols of liquid from the mouth and coming into contact with the dental workers.

OBJECTS OF THE INVENTION

A primary object of the present invention is to provide a protective apparatus that incorporates both physical and vacuum barriers in a medical or dental work environment.

Another object of the invention is to provide an apparatus that is of sufficient size to cover an entire site of a medical or dental procedure.

A further object of the invention is the destruction or disposal of harmful substances generated during a medical or dental procedure.

Still another object of the invention is to provide an apparatus that is portable and easily adjusted and transported to fit the requirements of each different usage.

Another further object of the invention is to provide an apparatus having a clear shield surrounded by apertures connected to a vacuum generating system and drawing fluids therethrough.

An additional object of the invention is to provide an apparatus which is relatively simple to use, inexpensive to produce and which is especially well adapted for the intended usage thereof.

Another object of the invention is to provide a method for isolating the immediate area around a dental, medical, laboratory, or industrial procedure site utilizing such an apparatus.

Other objects and advantages of this invention will become apparent from the following description taken in conjunction with the accompanying drawings as set forth, by way of illustration and example.

The drawings constitute a part of this specification and include exemplary embodiments of the present invention and illustrate various objects and features thereof.

BRIEF DESCRIPTION OF THE DRAWINGS

FIG. 5C shows the hydraulic jack inside the connector box shell of the invention.

FIG. 5D is a more detailed view of the jack inside the connector box shell of the invention.

FIG. 6C is another view of the vacuum tube of the invention.

SUMMARY OF THE INVENTION

Figure 1:
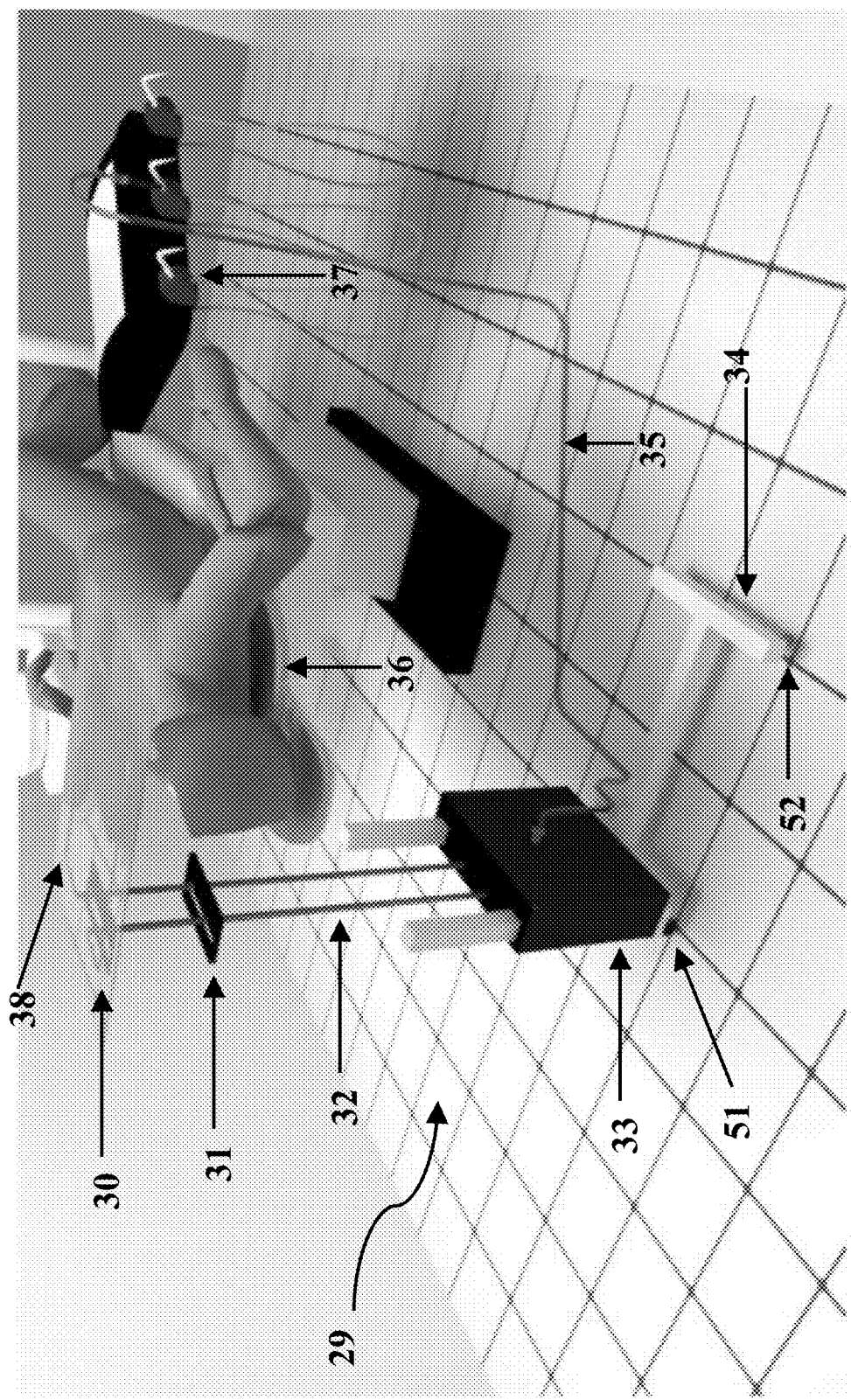
FIG. 1 is a pictorial view of the apparatus integrated with a dental chair in use with a patient in accordance with the present invention.

The invention is an ambidextrous piece of equipment that is placed between the healthcare provider and the patient. It will protect both patient and healthcare provider from aerosol droplets that can be acquired during diagnosis and treatment without limiting the operator's movement or field of vision. This piece of equipment requires no training and minimal maintenance. It can be freestanding or part of the dental chair unit. The freestanding unit can be transported from different working stations with its wheels. In between patients it can be wiped down clean or replaced by another barrier to save time. The height can be adjusted according to the preference of the operator or the procedure that is going to be performed. The suction is used to create a negative airflow away from the patient's mouth and nose.

The invention further provides a protective apparatus that incorporates both physical and vacuum barriers; to provide such an apparatus that is of sufficient size to cover an entire site of a medical or dental procedure, and provides for destruction or disposal of harmful substances; to provide such an apparatus that is portable and easily adjusted to fit the requirements of each different usage; to provide such an apparatus providing a clear protective shield surrounded by apertures connected to a vacuum generating system and drawing fluids therethrough; to provide such an apparatus which is relatively simple to use, inexpensive to produce and which is especially well adapted for the intended usage thereof; and to provide a method for isolating the immediate area around a medical, laboratory, or industrial procedure site utilizing such an apparatus.

The invention also provides a portable and height adjustable apparatus for reducing the potential for contamination of personnel during a dental procedure likely to produce both contaminated sprays and aerosols in an area of said procedure; said apparatus comprising: (a) a base with two wheels, said wheels spaced apart for easy transportation; (b) two horizontal rests having sufficient length for stability; (c) two adjustable telescopic parallel tubes with locking knobs that can be adjusted up or down vertically wherein said tubes are adjusted up or down by means of a hydraulic jack; (d) a rectangular metal frame that unites the two vertical tubes located at the superior part of the unit; (e) a clear vinyl tube placed along the superior metal frame, said vinyl tube having orifices spaced apart, said vinyl tube being connected to a dental chair unit for high suction; and (f) a transparent snap on shield barrier with or without magnification placed on top of the superior metal frame and adapted to be placed in a covering relationship to the area to be isolated to form said physical barrier there above.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The protective apparatus in accordance with the present invention and integrated with the dental chair and equipment as shown in FIG. 1 is generally designated by the reference numeral 29. The protective apparatus 29 generally comprises support structures 32, 33 and 34, a snap on transparent shield 30, pivotally mounted on the support structures 32, 33 and 34 and a vacuum drawing system 37. The vacuum drawing system 37 includes a vacuum conduit 35, a vacuum channel member 38 positioned about the shield 30, and a vacuum drawing system 37 flow connected to the channel member 38 by the vacuum conduit 35. The horizontal support structure 34 includes wheels 51 and an anterior break stabilizer 52. On the inside of the support structure 33 there is a hydraulic jack (not shown) for adjusting as required the height of the transparent shield 30.

Figure 2:
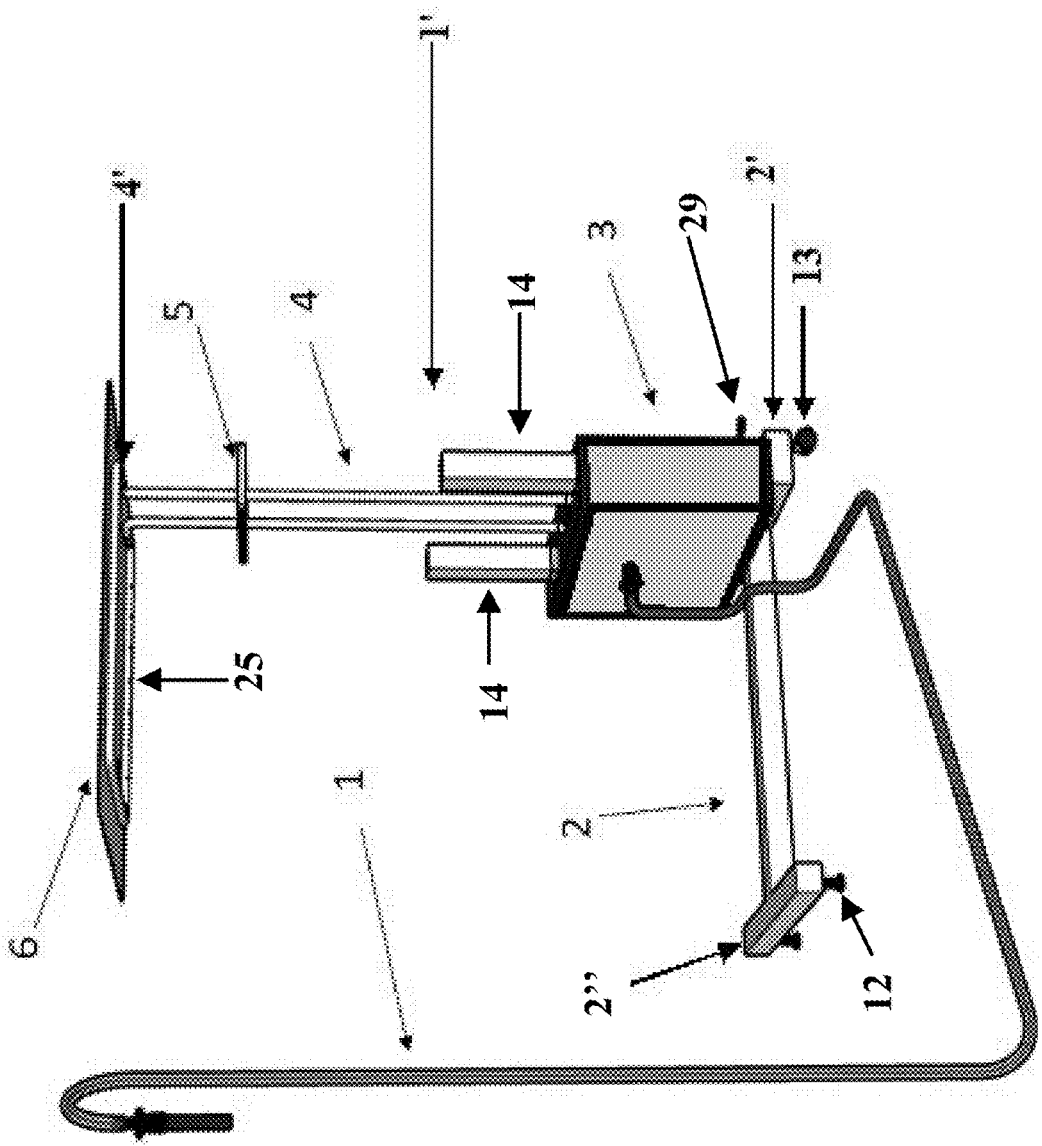
FIG. 2 is an enlarged perspective view of the apparatus showing all the required elements including a transparent shield thereof in a generally horizontal orientation.

Referring to FIG. 2 of the invention, the apparatus 1' of the invention includes a vacuum hose 1, a horizontal body 2 including two horizontal rests 2' and 2" of a suitable length for stability, a vertical body 14, a connector box 3 which includes inside a hydraulic jack (not shown) sitting on horizontal rest 2' and having jack lever 29, a vertical telescoping tube 4 that includes a horizontal section 4', a handle 5 and a protective shield as a transparent sheet 6 on top of horizontal section 4' which said tube horizontal section including orifices 25. Horizontal rest 2' includes wheels 13 while horizontal rest 2" includes an anterior break stabilizer 12. The connector box 3 moves up and down by means of the hydraulic jack along the two vertical stabilizers 14.

Figure 2A:
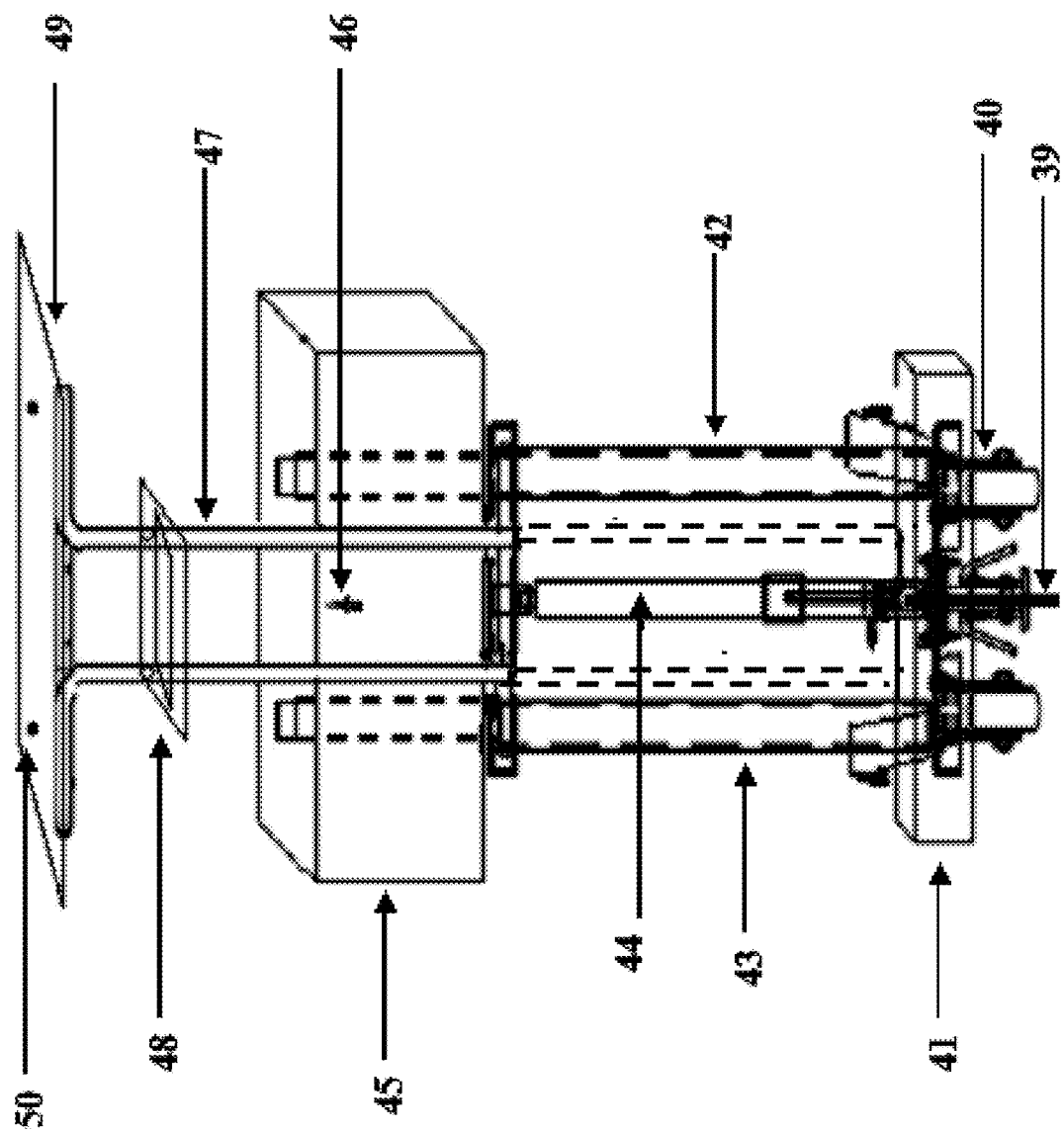
FIG. 2A is a perspective view of the apparatus as seen from the back side showing the elements of the invention including the hydraulic jack holding the connector box in the up position.

FIG. 2A is another perspective view which further illustrates the innerworkings of the connector box. The apparatus as shown in FIG. 2A includes horizontal rest 41 with wheels 40. On top of the horizontal rest 41 there is the vertical body stabilizers 42 and 43 and hydraulic jack 44. The hydraulic jack 44 including a jack lever 39 would be on the horizontal body 41 of the base, and the connector box 45 moves up or down along the two vertical stabilizers 42 and 43 of the base. The tubing 47 would move with the connector box up and down. The apparatus as shown in FIG. 2A further includes vacuum tube connector 46, handle 48, and transparent shield 49 having clasp 50.

Figure 2C:
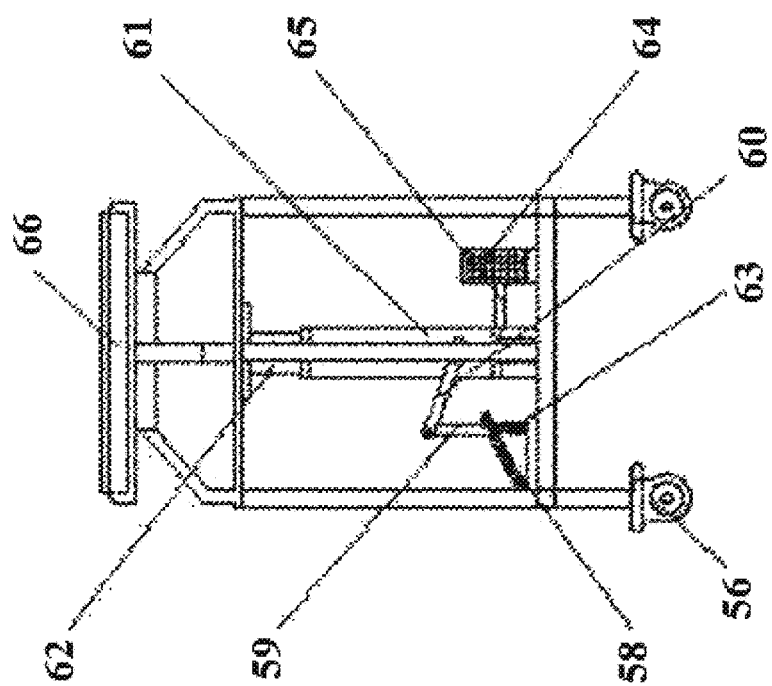
FIG. 2C is a another view related to the one shown in FIG. 2B.
Figure 2B:
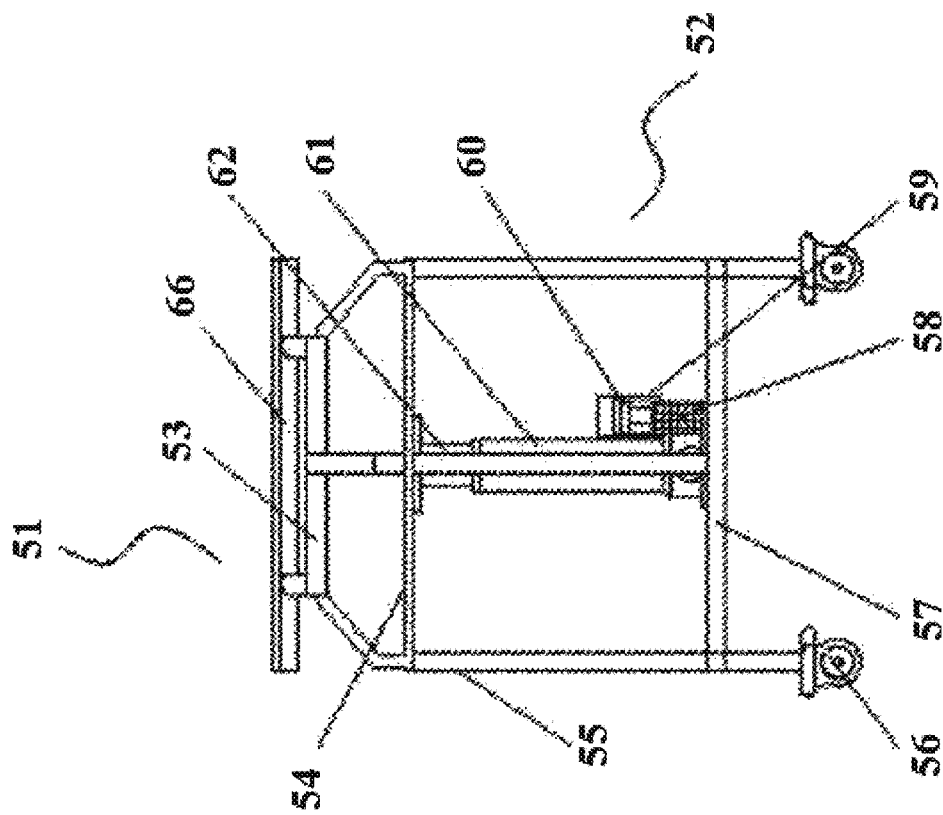
FIG. 2B is another view showing the action of an hydraulic jack on lifting the tray having medical instruments.

FIG. 2B shows an embodiment of a foot-controlled hydraulic surgical instrument table with adjustable height, including a housing assembly 51 and a lifting assembly 52. The housing assembly 51 includes a tray 52 and a connecting frame 53, a lifting frame 54, supporting column 55, universal wheel 56 and supporting plate 57. The supporting column 55 penetrates the upper surface of the supporting plate 57 longitudinally and is fixedly connected to the supporting plate 57. The lifting frame 54 is installed on the upper surface of the supporting column 55, and it is slidably connected to the support column 55. The universal wheel 56 is arranged on the lower surface of the support column 55 and is fixedly connected to the support column 55. The connecting frame 53 is arranged above the lifting frame 54 and is fixedly connected to the lifting frame 54. The tray 52 is arranged on the upper surface of the connecting frame 53 and is detachably connected to the connecting frame 53. The lifting assembly 52 includes a rising pedal 58, a connecting rod 59, a lever handle 60, a hydraulic jack 61, a piston rod 62, a spring 63, a descending pedal 64 and a driven frame 65. The ascending pedal 58 is installed on the upper surface of the support plate 57, and is rotatably connected with the support plate 57. The spring 63 is arranged on the lower surface of the rising pedal 58 and is fixedly connected to the rising pedal 58. The connecting rod 59 is arranged on the outer side wall of the rising pedal 58 and is fixedly connected to the rising pedal 58, and the lever handle 60 is installed on the outside of the connecting rod 59. The hydraulic jack 61 is installed on the upper surface of the support plate 57 and is close to the left side of the rising pedal 58. The hydraulic jack 61 and the support plate 57 are fixedly connected, and the piston column 62 is set on the upper surface of the hydraulic jack 61. The lowering pedal 64 is arranged on the upper surface of the driven frame 65 and is close to the rear of the hydraulic jack 61. The lowering pedal 64 is rotatably connected with the supporting plate 57, and one end of the driven frame 65 is connected to the lower pedal 64 which is fixedly connected, and one end of the driven frame 65 is fixedly connected to the hydraulic jack 61.

In FIG. 2C embodiment, the medical staff places the body of the surgical instrument table at the working place, and the medical staff can step on the ascending pedal 58. The ascending pedal 58 drives the connecting rod 59 to descend, thereby driving the lever handle 60 to descend, and then the elastic force of the spring raises the pedal 58. Return to the original position, requires driving the lever handle 60 to rise, and the medical staff continues to step on the rising pedal to achieve the effect of controlling the piston column 62 to continuously rise with their feet. The piston column 62 rises and lifts the lifting frame 54 and the connecting frame 53 to rise. Therefore, the height of the tray 66 is raised, and the medical staff adjusts the angle of the descending pedal 64 with their feet, so that the oil discharge check valve on the hydraulic jack 61 can be rotated, so as to achieve the effect of controlling the lowering of the piston rod 62 with the foot, thereby making the tray height 66 to drop.

Figure 3:
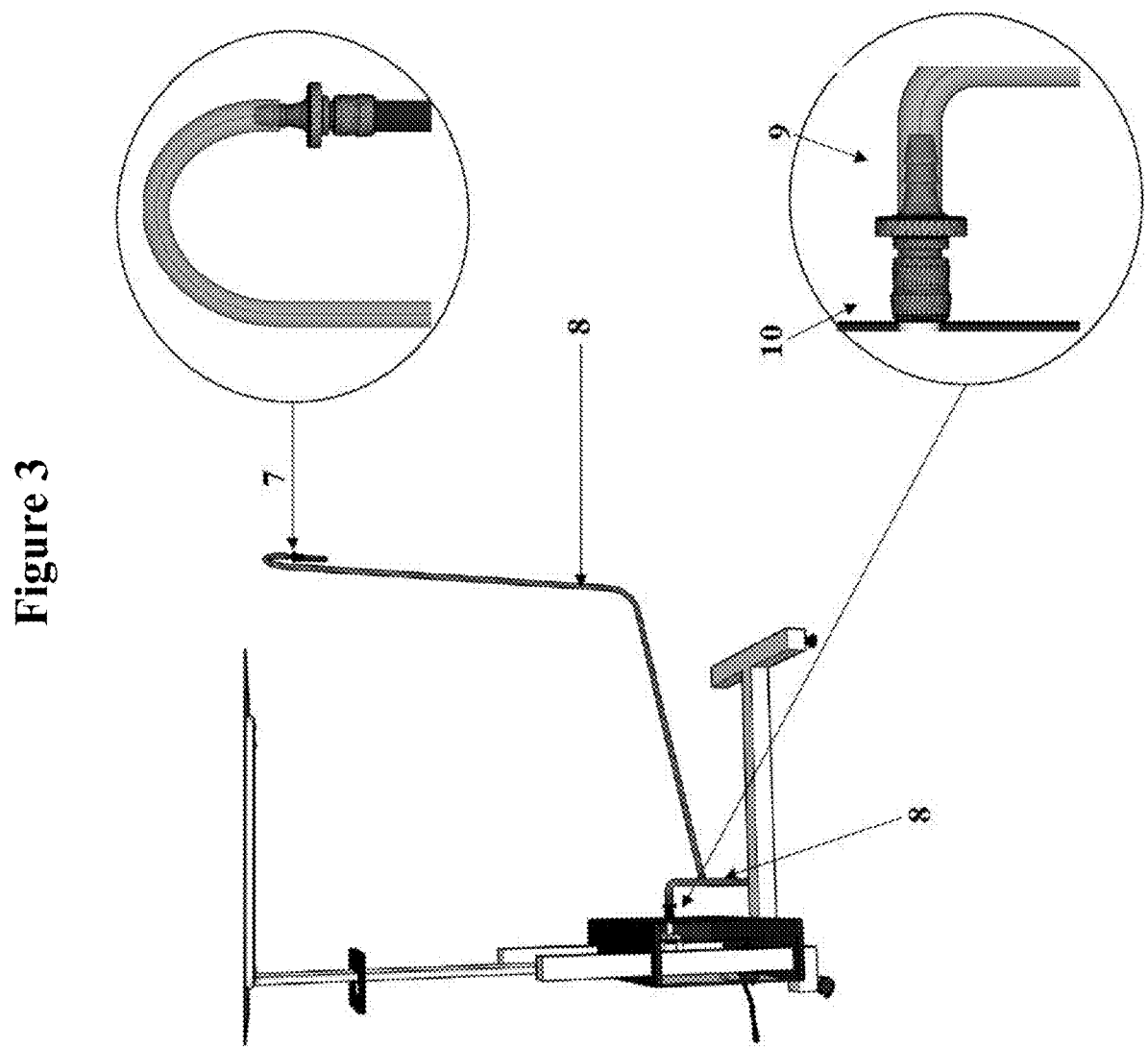
FIG. 3 is a detailed view of the vacuum hose attached to the apparatus of the invention.

As shown in FIG. 3, the flexible vacuum hose 8 includes a vacuum plug 7 shown as an exploded view, and a vacuum female connector 9 connected to male member 10.

Figure 4:
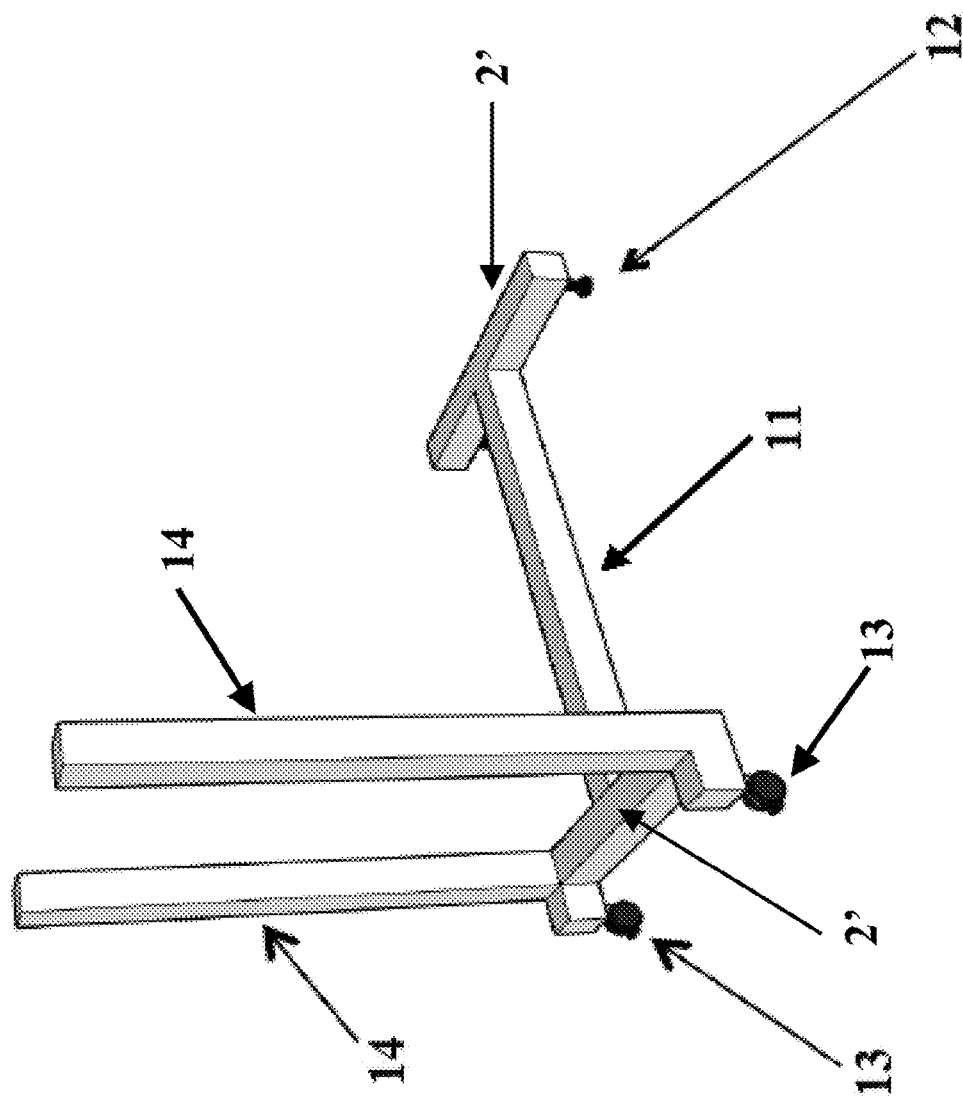
FIG. 4 is a perspective view of the base portion of the apparatus of the invention.

In FIG. 4 there is a more detailed view of the horizontal body shown in FIG. 2. The horizontal body of the base is shown as reference numeral 11, which includes an anterior break stabilizer 12, wheels 13 and a vertical body 14 on base 11.

Figure 5B:
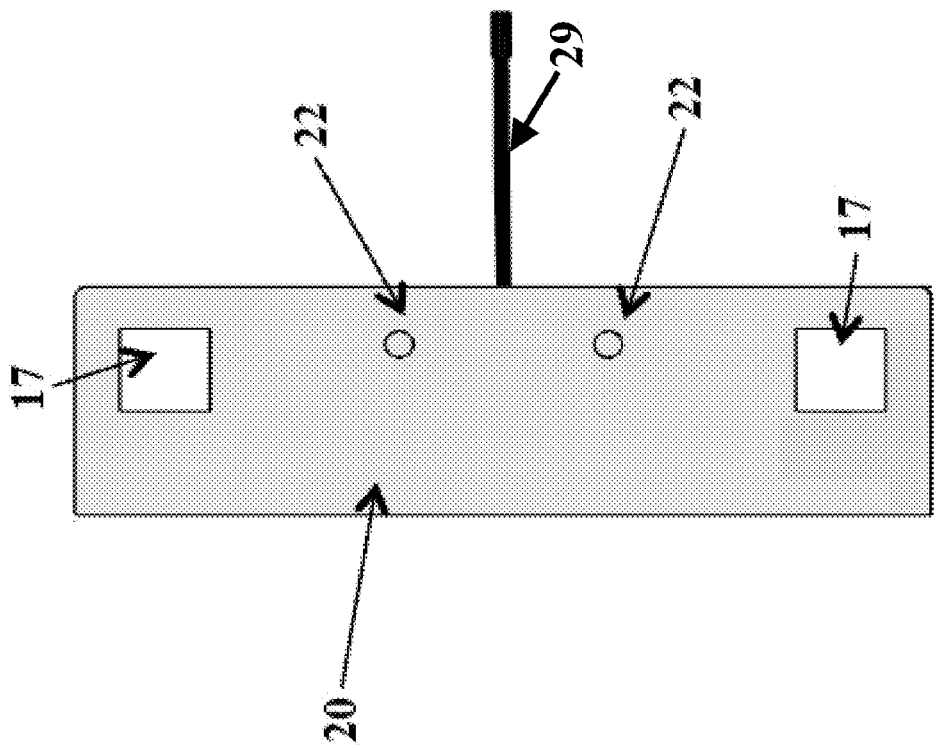
FIG. 5B illustrates the top portion of the connector box shell shown in FIG. 5A.
Figure 5A:
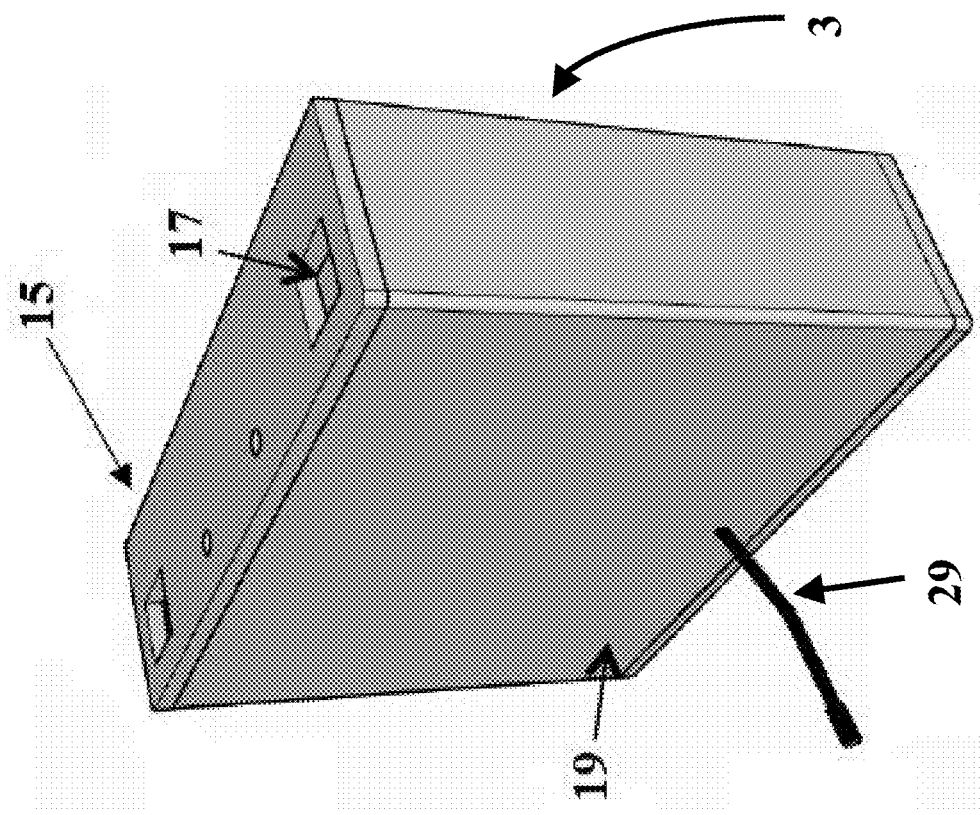
FIG. 5A is a schematic view of the connector box shell of the invention.

In FIG. 5A, there is shown the connector box 3 that includes an outside shell 15, orifices 17 for sliding through the vertical stabilizers, a back side of shell jack lever 19 and jack lever 29. The hydraulic jack would be on the horizontal body of the base, and the connector box moves up or down along the two vertical stabilizers of the base. The tubing would move with the connector box up and down.

FIG. 5B shows a top view 20 of shell 15 featuring orifices 22 for the vertical metal tubing, orifices 17 for sliding the vertical stabilizers and jack lever 29.

FIG. 5C illustrates the inside look of connector box 3 which includes a hydraulic jack 16 and jack lever 29.

FIG. 5D is another view of the connector box showing the front side of the shell 18, the hydraulic jack 16, the side view 21 of the shell, the back side of the shell jack lever 19, and jack lever 29.

Figure 6A:
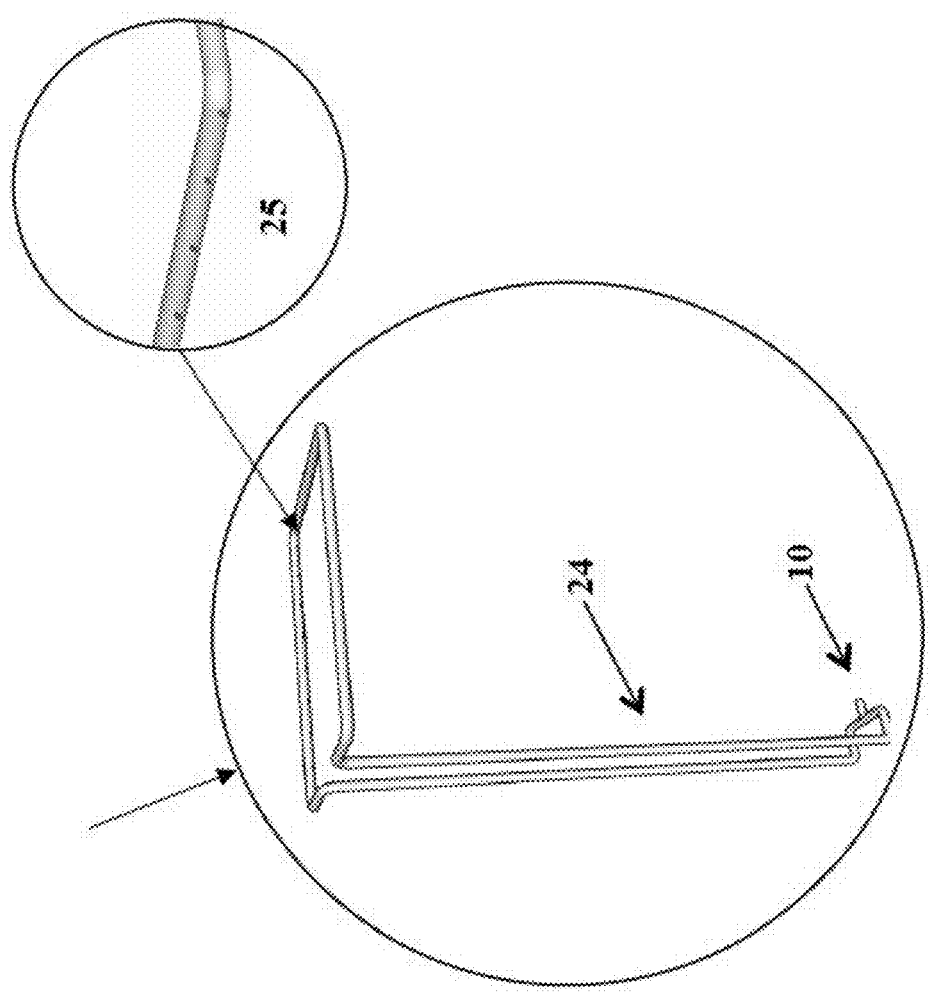
FIG. 6A is a schematic view of the copper vacuum tube of the invention.
Figure 6B:
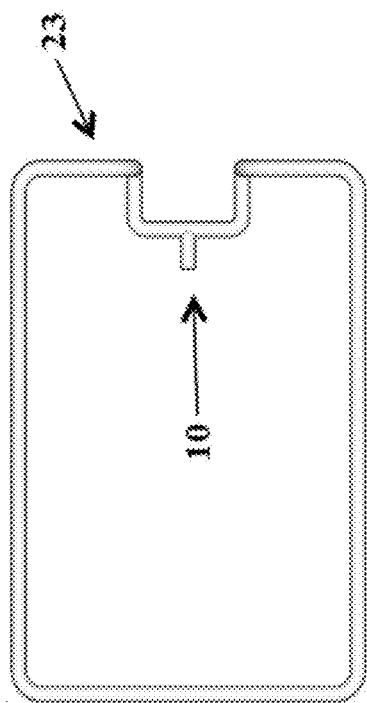
FIG. 6B shows a view of the lower section of the vacuum tube of the invention.

FIG. 6A is a detailed view of the vertical metal tubing of FIG. 2, illustrating the vertical tubing 24 including a top horizontal section 23 that includes orifices 25 and as further shown in FIG. 6B a lower section having a vacuum male connector 10.

FIG. 6C is another detailed view of the metal tubing 24 with horizontal section 23 and lower section showing the vacuum male connector 10.

Figure 7B:
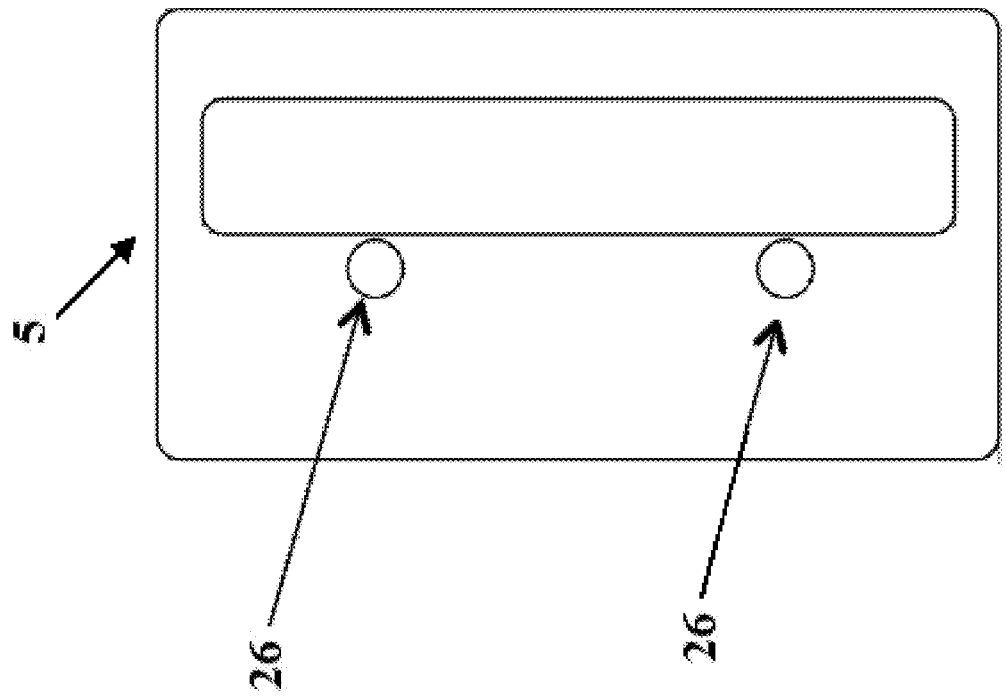
FIG. 7B is another view of the handle of the invention.
Figure 7A:
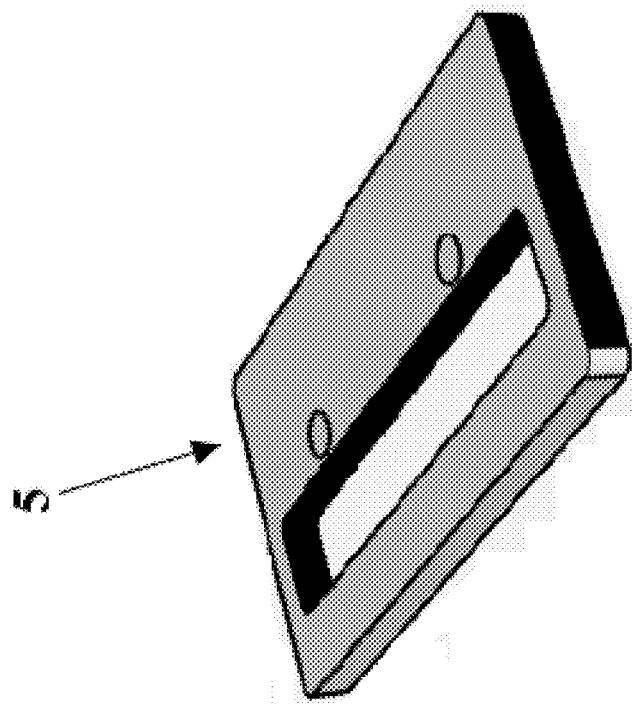
FIG. 7A illustrates the handle of the apparatus of the invention.

FIG. 7A is a pictorial view of handle 5 and FIG. 7B shows the handle 5 illustrating orifices 26 for the vertical tubing.

Figure 8B:
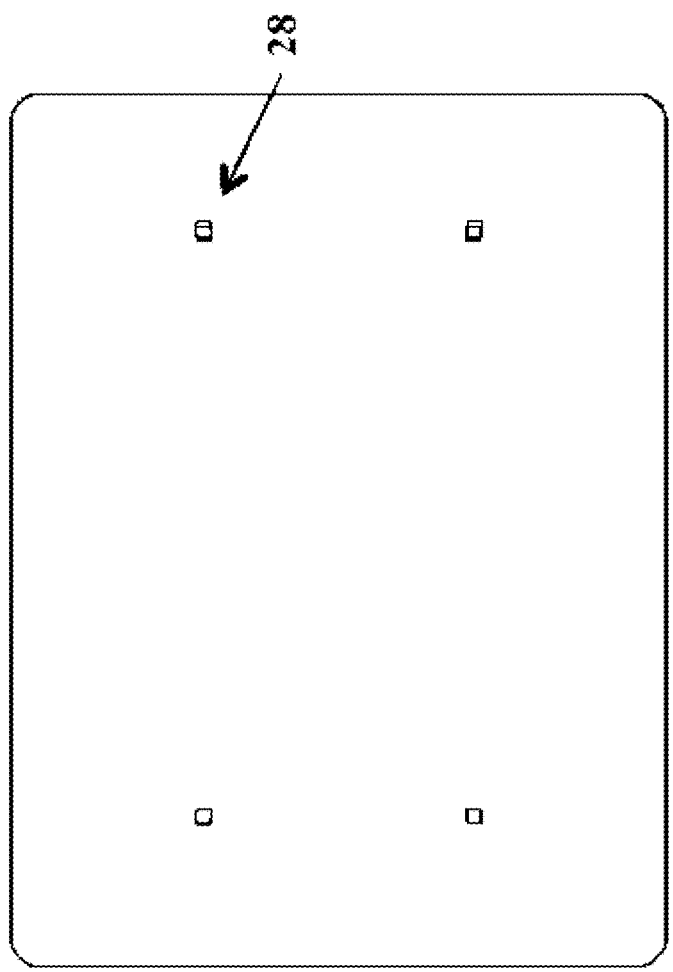
FIG. 8B illustrates the transparent protector of FIG. 8A having plastic clasps.
Figure 8A:
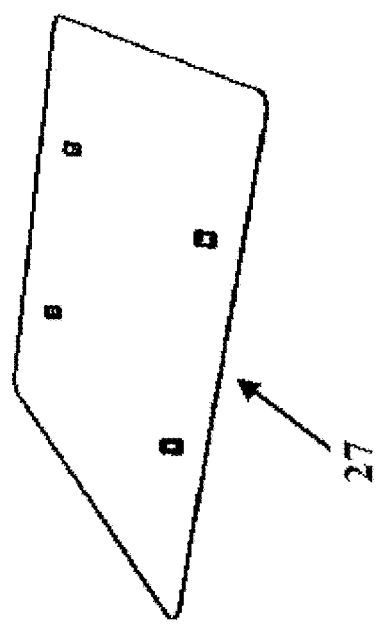
FIG. 8A features an acrylic plastic transparent protector.

FIG. 8A illustrates a transparent protector sheet 27 typically made from polymers such as acrylic polymers.

FIG. 8B shows a transparent protector/shield sheet having clasps 28.

The freestanding apparatus 1' of the invention shown in FIG. 2 includes the following elements: A base 2 with two wheels 13 (only one shown) spaced apart a suitable distance for easy transportation; two horizontal rests 2' of a suitable length for stability; two telescopic parallel tubes 4 with locking knobs (not shown) that can be adjusted vertically for height. At the superior part of the unit there is a rectangular metal frame 4' with orifices for suction that unites the two vertical tubes, this frame being of suitable dimensions. Along this superior metal frame 4' one may run along the length of the frame a clear vinyl tube, of suitable inner diameter, with orifices two inches apart, that is connected to dental chair unit for high suction. Similarly the metal frame in form of tubular geometry may have orifices 25 for suction. On top of the superior metal frame there is a transparent snap on barrier 6 with or without magnification.

The protective apparatus in accordance with the present invention as shown in FIG. 2 is generally designated by the reference numeral 1'. The protective apparatus 1' generally comprises a support structure 2, a transparent shield 6, pivotally mounted on the support structure 4, and a vacuum drawing system 1. The vacuum drawing system 1 includes a vacuum conduit, a vacuum channel member positioned about the shield 6, and a vacuum generator flow connected to a channel member by the vacuum conduit.

The support structure as shown in FIG. 4 includes a horizontal body of the base, which is shown as reference numeral 11, which includes an anterior break stabilizer 12, wheels 13 and a vertical body 14 on base 11. The support structure further includes two horizontal rests 2' of a suitable length for stability.

The transparent shield 6 of the invention is preferable substantially rectangular and has a planar surface constructed of rigid, transparent plastic, see FIG. 2, FIG. 8A and FIG. 8B.

The rectangular dimensions of the shield 6 generally are greater than the dimensions of the exterior of the tubular member 4'. The shield 6 is preferably sized to cover and contain the spread of harmful substances foreseeably emanating under pressure or propelled from a surgical incision or the like toward the upper body and face of a surgeon or dentist, while simultaneously allowing personnel generally unobstructed working access with their hands to an incision or other working site on a patient. See FIG. 1. It is foreseen that the invention could be embodied in a variety of other sizes for additional applications.

In use the apparatus 1' is positioned over a patient, having a medical or dental procedure or the like performed thereon, as shown in FIG. 1 and FIG. 2. The angle height and horizontal position of the shield may be adjusted to help protect the surgeon or dentist or nurse. A pump (not shown) is started to draw substances, especially gases and aerosols containing body fluids, from under the shield 6 into the orifices 25 (See FIG. 2) and subsequently through the channels and vacuum conduit and finally through the pump with solids and liquids having been removed therefrom so as to draw such substances away from the surgeon or dentist, thereby substantially reducing the risk of exposure of the surgeon's or dentist mucous membranes and the like to such substances. The shield 6 also operatively prevents sprays or substances propelled with force from the site of the patient's operational procedure from striking the surgeon or dentist in an unprotected area, while allowing the surgeon or dentist to be able to clearly see the operational site and to work with their hands in a generally unobstructed manner at the site. In particular, the site is generally easily accessible from many directions.

In a specific example having specific dimensions, the freestanding apparatus of the invention includes the following elements: A base with two wheels approximately 20 inch apart for easy transportation; two horizontal rests approximately 16 inches long for stability; two adjustable telescopic parallel tubes with locking knobs that can be adjusted vertically from 34-56 inches. At the superior part of the unit there is a rectangular metal frame that unites the two vertical tubes, this frame is approximately 12.8-19.8 inches. Along this superior metal frame is a clear vinyl tube, a quarter inch inner diameter, with orifices two inches apart, that is connected to dental chair unit for high suction. This horizontal frame presents orifices that are approximately 2 inches apart. This is connected to the vertical tubes 4 that is connected to a vinyl tubing 1 to the chair's high suction as shown in FIG. 2. On top of the superior metal frame is a transparent snap on barrier with or without magnification.

The content of all references cited in the instant specification and all cited references in each of those references are incorporated in their entirety by reference herein as if those references were denoted in the text While the many embodiments of the invention have been disclosed (Angres) above and include presently preferred embodiments, many other embodiments and variations are possible within the scope of the present disclosure and in the appended claims that follow. Accordingly, the details of the preferred embodiments and examples provided are not to be construed as limiting. It is to be understood that the terms used herein are merely descriptive rather than limiting and that various changes, numerous equivalents may be made without departing from the spirit or scope of the claimed invention.

What is claimed is:

1. A portable and height adjustable apparatus for reducing the potential for contamination of personnel during a medical or dental procedure likely to produce both contaminated sprays and aerosols in an area of said procedure; said apparatus comprising:
   (a) a horizontal base with two wheels, said wheels spaced apart for easy transportation;
   (b) two horizontal rests having sufficient length for stability;
   (c) two adjustable telescopic parallel tubes with locking knobs located at the superior part of the apparatus that can be adjusted up or down vertically and wherein said parallel tubes are adjusted up or down by means of a hydraulic jack; and
   (d) a rectangular metal frame that unites the two parallel tubes located at the superior part of the apparatus.

2. The apparatus according to claim 1, wherein said shield is substantially planar and is constructed of rigid material.

3. The apparatus according to claim 2, wherein said shield is made of acrylic or methacrylic polymers and copolymers.

4. The apparatus according to claim 2, wherein said shield is made of polycarbonate polymers and copolymers.

5. The apparatus according to claim 1, wherein the rectangular metal frame that unites the two parallel tubes includes a plurality of apertures spaced there along.

6. The apparatus according to claim 5, further including a vacuum drawing conduit extending substantially around a perimeter of said shield.

7. The apparatus according to claim 6, having a vacuum generating pump operably connected to said vacuum drawing conduit for drawing fluids through said apertures from beneath said shield.

8. The apparatus according to claim 1, further including a transparent snap on shield barrier with or without magnification placed on top of the rectangular metal frame and adapted to be placed in a covering relationship to form said shield barrier there above.

9. The apparatus according to claim 1, wherein a clear vinyl tube is placed along the rectangular metal frame, said vinyl tube having orifices spaced apart, said vinyl tube being connected to a dental chair unit for high vacuum suction.

10. A freestanding apparatus useful for performing dental procedures comprising:
(a) a base with two wheels, said wheels spaced apart for easy transportation;
(b) two horizontal rests having sufficient length for stability;
(c) two adjustable telescopic parallel tubes with locking knobs located at the superior part of the apparatus that can be adjusted up or down vertically;
(d) a rectangular metal frame, with multiple orifices, that unites the two vertical tubes located at the superior part of the apparatus;
(e) a clear vinyl tube placed along the rectangular metal frame, said vinyl tube having orifices spaced apart, said vinyl tube being connected to a dental chair unit for high vacuum suction; and
(f) a transparent snap on barrier shield with or without magnification placed on top of the rectangular metal frame.

11. The apparatus according to claim 10, wherein said shield is substantially planar and is constructed of rigid material.

12. The apparatus according to claim 11, wherein said shield is made of acrylic or methacrylic polymers and copolymers.

13. The apparatus according to claim 11, wherein said shield is made of polycarbonate polymers and copolymers.

14. The apparatus according to claim 10, further including a vacuum drawing conduit extending substantially around a perimeter of said shield.

15. The apparatus according to claim 10, having a vacuum generating pump operably connected to said vacuum drawing conduit for drawing fluids through said apertures from beneath said shield.

* * * * *